United States Patent
Bornzin et al.

(10) Patent No.: US 7,606,618 B1
(45) Date of Patent: Oct. 20, 2009

(54) IMPLANTABLE MEDICAL DEVICE WITH NOTIFICATION SYSTEM

(75) Inventors: Gene A. Bornzin, Simi Valley, CA (US); Peter Boileau, Valencia, CA (US); Paul A. Levine, Santa Clarita, CA (US); Corey L. Brown, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 546 days.

(21) Appl. No.: 11/400,114

(22) Filed: Apr. 7, 2006

(51) Int. Cl.
*A61N 1/00* (2006.01)
(52) U.S. Cl. .......................................... 607/27
(58) Field of Classification Search .................. 607/27, 607/19, 29, 71; 600/508, 515, 516, 510
See application file for complete search history.

(56) References Cited

U.S. PATENT DOCUMENTS

| | | | |
|---|---|---|---|
| 4,055,189 A | 10/1977 | Auerbach et al. | 128/419 PG |
| 4,295,474 A | 10/1981 | Fischell | 128/697 |
| 4,488,555 A | 12/1984 | Imran | 128/419 PT |
| 4,556,061 A | 12/1985 | Barreras et al. | 128/419 PT |
| 5,476,483 A | 12/1995 | Bornzin et al. | 607/17 |
| 5,549,653 A | 8/1996 | Stotts et al. | 607/4 |
| 5,607,459 A * | 3/1997 | Paul et al. | 607/29 |
| 5,609,614 A * | 3/1997 | Stotts et al. | 607/29 |
| 5,609,615 A | 3/1997 | Sanders et al. | 607/36 |
| 5,628,776 A | 5/1997 | Paul et al. | 607/119 |
| 5,643,328 A | 7/1997 | Cooke et al. | 607/36 |
| 5,709,712 A | 1/1998 | Paul et al. | 607/27 |
| 5,814,088 A | 9/1998 | Paul et al. | 607/28 |
| 5,893,881 A | 4/1999 | Elsberry et al. | 607/5 |
| 6,080,187 A * | 6/2000 | Alt et al. | 607/32 |
| 6,480,744 B2 | 11/2002 | Ferek-Petric | 607/60 |
| 2002/0099424 A1 | 7/2002 | Ferek-Petric | 607/60 |
| 2003/0050566 A1 * | 3/2003 | Ujhelyi et al. | 600/515 |

FOREIGN PATENT DOCUMENTS

| | | |
|---|---|---|
| WO | WO 97/43003 | 11/1997 |
| WO | WO 98/03222 | 1/1998 |
| WO | WO 98/42406 | 10/1998 |

* cited by examiner

*Primary Examiner*—George Manuel
*Assistant Examiner*—Robert N Wieland

(57) ABSTRACT

An implantable medical device with a notification system. The device monitors itself and an implantee for one or more condition indicating notification and delivers the notification at a time the patient is determined to be wakeful and, optionally, at relative rest. The notification can be repeated periodically until acknowledged by the user or the system is evaluated and reprogrammed by the physician. A user input can be included to provide the device confirmation of receipt of the notification as well as to delay delivery of any indicated subsequent notifications. The notification is provided without requiring any additional or special dedicated hardware.

12 Claims, 7 Drawing Sheets

IMPLANTABLE MEDICAL DEVICE WITH NOTIFICATION SYSTEM

FIELD OF THE INVENTION

The invention relates to the field of implantable medical devices and, in particular, to an implantable medical device with a notification system to conveniently and efficiently notify the patient of certain conditions, such as detection of tachycardia or a change in the device operation or condition.

BACKGROUND OF THE INVENTION

Implantable medical devices have been developed to provide ongoing monitoring of the physiological state of a patient and, when indicated, automatically provide therapy for detected conditions. One particular type of implantable medical device is a pacemaker which can be combined with an implantable cardioverter-defibrillator (ICD) which can automatically monitor the patient's cardiac activity and provide therapeutic pacing stimulation for bradycardia and tachycardia conditions as well as a defibrillating shock upon detection of a fibrillation condition. Such implantable devices typically comprise a microprocessor-based controller, a pulse generation circuit operating under control of the microprocessor, and one or more sensing and stimulation electrodes which are typically implanted in contact with the patient's cardiac tissue and are connected to the implantable device via one or more leads. The devices are also typically capable of self-monitoring by detecting a variety of conditions of the implantable device itself.

There are times when it is desirable to alert the patient of certain conditions which the device may detect, such as detection of a change in device operation or detection of certain physiological conditions. Examples of such situations include: a change in capture threshold, failure of a lead or other component of the device, and an increase in the number of pacemaker-mediated tachycardia (PMT) responses indicating possibly inappropriate programming. These conditions may not be noticeable to the patient yet may still indicate that further intervention or reprogramming of the implanted device would be warranted. For example, the patient may need to arrange a visit with an attending clinician to reprogram/repair/service the device or to modify or begin a medication regimen.

In the particular example of implantable defibrillators, as delivery of therapy can be physically and psychologically traumatic to the patient, it is sometimes deemed preferable to alert the patient to the prospect of the eminent delivery of therapy. One example of the desirability of this is that, in the case of ventricular tachycardia/ventricular fibrillation (VT/VF) patients, detection of such a tachycardia condition may precede a syncopal episode. In such a case, the patient could be alerted/advised to sit, recline, or take other action to avoid potential injury, such as pull to the side of the road if driving.

In the particular case of atrial tachycardia/fibrillation (AT/AF) patients, some of these AF patients do not consciously notice when they enter into an AF episode. Therefore, they are not aware of the condition or that they could benefit from treatment, such as administration of medication. According to published literature, up to one third of patients with clinically recognized AF have what is known as silent AF, e.g. they are unaware of ongoing AF episodes at least part of the time. Further, Holter and transtelephonic monitoring also indicates that for patients with paroxysmal AF (PAF), at least ninety percent of AF episodes are asymptomatic.

It has long been recognized that episodes of AF tend to contribute to further ongoing episodes of AF. Atrial fibrillation and atrial flutter are also known to increase the risk of thromboembolism. Thus, many physicians believe it is best to maintain sinus rhythm as much as possible in patients with episodes of persistent AF via, for example, administration of electrical and/or pharmacological cardioversion. Anticoagulation medication is also a standard therapy for chronic AF and PAF patients, particularly before and after pharmacological or electrical cardioversion. Accordingly, these patients would benefit from a system to make them consciously aware of their arrhythmia so that they may seek appropriate treatment, e.g. administration of anticoagulation medication and/or electrical or pharmacological cardioversion.

Implantable medical devices, such as implantable cardiac stimulators, are known which provide alerts or other warning signals to notify the patient of certain conditions. However, several shortcomings exist in the prior art, especially as would relate to alerting patients of silent AF. These shortcomings include the requirement for special dedicated electrodes for providing notification in addition to electrodes otherwise required by the implantable device which add to the cost and complicate the implant procedure. Also, conditions indicating a notification may occur at a time at which the patient is not in a condition to readily notice such a notification, such as during sleep or strenuous physical activity and notifications provided at the time of occurrence may go unnoticed. Further, a notification may be noticed but, as no input is provided to the device if appropriate corrective action has been taken, it remains indeterminate whether subsequent reminder notifications are indicated or not.

Thus, it will appreciated that there is an ongoing need for an implantable medical device which can effectively provide notification to a patient upon detection of conditions indicating notification, such as detection of a silent AF or a change in device operation or condition. There is a need for an implantable medical device with notification features that avoids the need for special or separate structures, such as a notification electrode. There is a need for an implantable medical device which can notify the patient in a manner and at a time selected to increase the likelihood that the patient will notice the notification. There is also a need for an implantable medical device that can monitor for corrective action taken and provide subsequent follow-up notifications as indicated. There is also a need for an implantable medical device where the patient can delay notifications when desired. There is also a need for an implantable medical device which can provide notification in the presence of R-waves and premature ventricular complexes (PVCs).

SUMMARY

An implantable medical device is disclosed comprising a controller, at least one sensing electrode providing sensed signals to the controller, a stimulation pulse generator receiving control signals from the controller, and at least one stimulation electrode connected to the stimulation pulse generator to provide indicated stimulation therapy wherein the controller evaluates the signals received from the at least one sensing electrode and, upon determination that at least one condition indicating notification has existed and that a desirable state for receipt of a notification signal exists, induces the device to deliver the notification signal.

In one embodiment, the desirable state comprises a waking state of a patient and the desirable state can further comprise an absence of strenuous physical activity.

In one embodiment, when the device determines that the at least one condition indicating notification has existed but the desirable state does not exist, the device delays delivery of the notification signal until such time as the device determines that the desirable state exists.

In one embodiment, the device can deliver multiple notification signals over a period of time corresponding to a given notification condition and can further comprise at least one user input in communication with the controller wherein activation of the at least one user input inhibits subsequent delivery of notification signals corresponding to the given notification condition. In one embodiment, activation of the at least one user input delays delivery of subsequent notification signals until after a determined period. The determined period can comprise a period of observed patient sleep and can comprise a programmable parameter.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
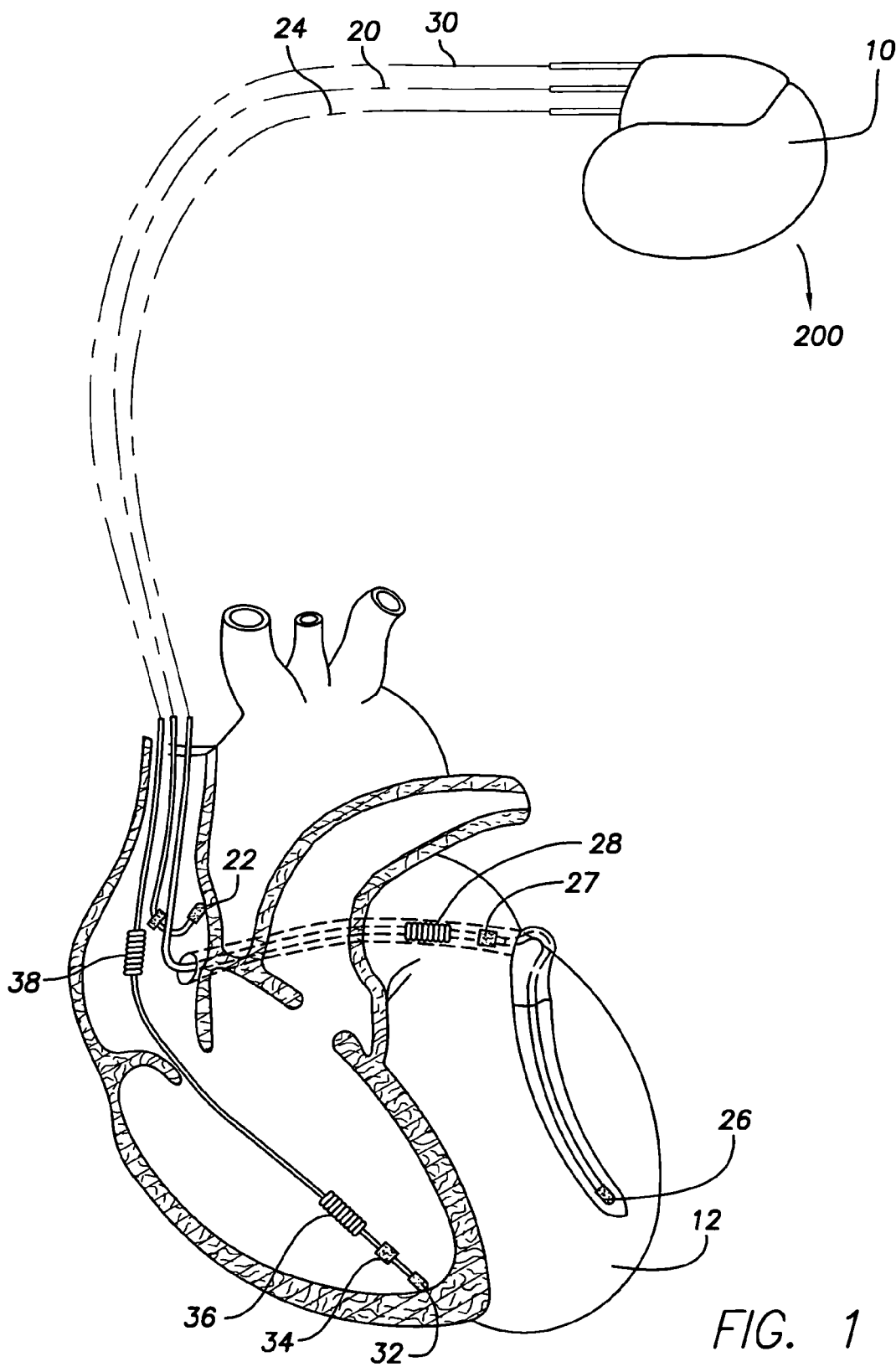
FIG. 1 is a simplified diagram illustrating an implantable stimulation device in electrical communication with at least three leads implanted into a patient's heart for delivering multi-chamber stimulation and shock therapy.

As shown in FIG. 1, there is an implantable stimulation device 10 with a notification system, referred to hereafter as "device 10" for brevity, in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
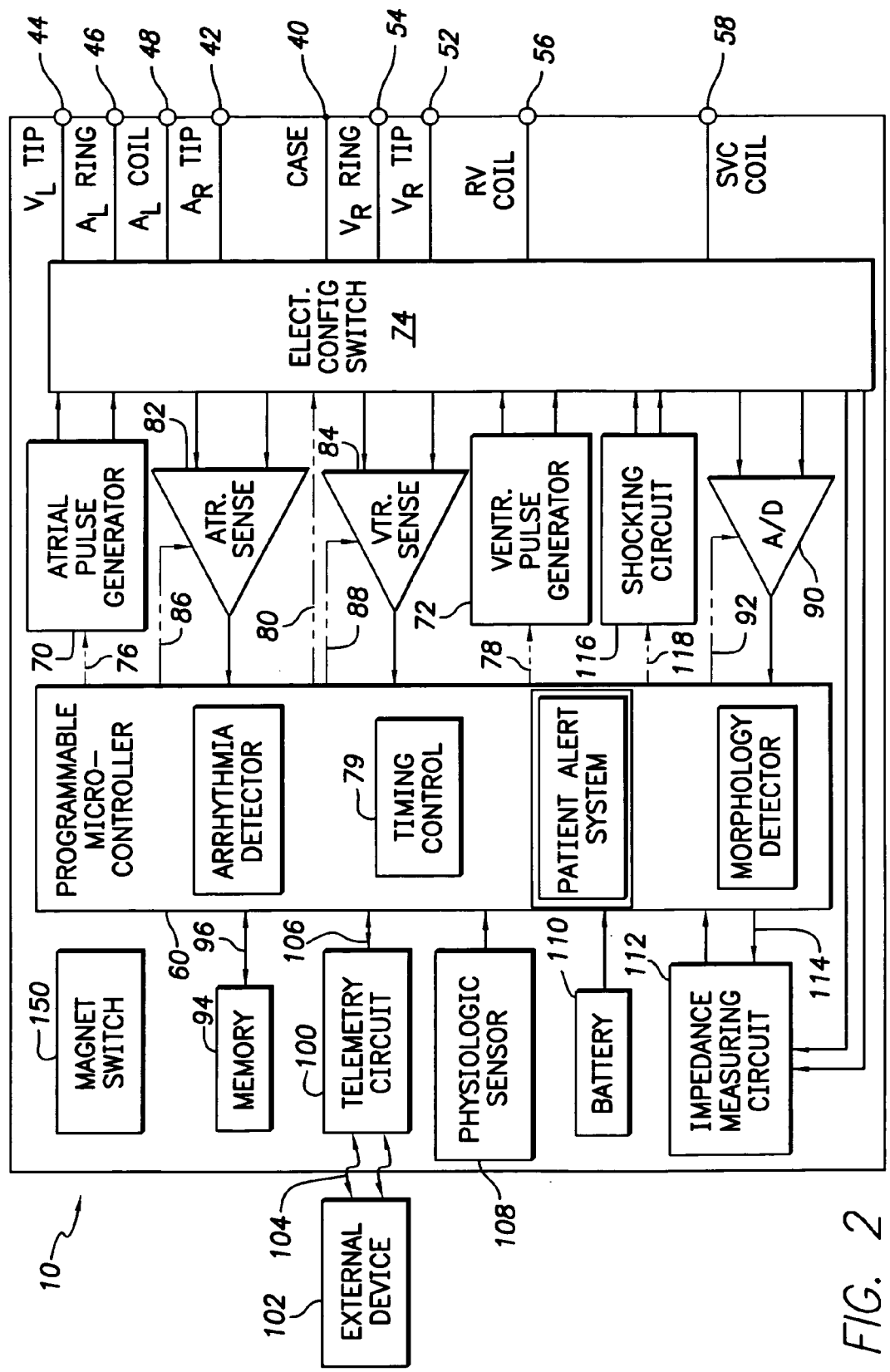
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

A housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic sensing control, bandpass filtering, and a threshold detection circuit, as known in the art, to selectively sense the cardiac signal of interest. The automatic sensing control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102, which, in certain embodiments, comprises a programmer. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, desired operating parameters or other programming instructions of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 may be activated from a standby condition in response to an indication from a radio frequency (RF) detector (not shown) that signals of a predetermined strength are being received. The telemetry circuit 100 can communicate with the microcontroller 60 via a communication link 104.

The telemetry circuit 100 also advantageously allows intracardiac electrograms (IEGMs) and status information relating to the operation of the device 10 (as contained in the microcontroller 60 or memory 94) to be sent to the external device 102 through an established communication link 104 as well as data from the sensor 108. In certain embodiments, data from the sensor 108 is selectively sent continuously via the communication link 104 and, in alternative embodiments, the data from the sensor 108 is sent in frames and/or as a derived signal, e.g. an average or rate.

The physiologic sensor 108 is commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

While shown in FIG. 2 as being included internal to the stimulation device 10, it is to be understood that the physiologic sensor 108 may also be positioned outside and in communication with the stimulation device 10 and may include a variety of sensors 108 some or all of which may be external to the device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. It is also to be understood that, in certain embodiments, the sensor 108 is capable of sensing multiple parameters and providing all the sensed parameters or a selected number of the parameters to the device 10.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the invention and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11-40 joules), as controlled by the microcontroller 60. Such shocking pulses are applied to the patient's heart 12 through at least two shocking electrodes and, as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Embodiments of the invention will now be described in greater detail with reference to FIGS. 3-6. Embodiments of the invention include a device 10 with a notification system that effectively provides notification signals 200 (FIG. 1) to a patient and/or attending clinical personnel in a variety of manners and circumstances as described below. The invention takes advantage of embodiments of an invention described in U.S. application Ser. No. 09/669,581 filed Sep. 26, 2000 entitled "Method and Apparatus for Alerting a Patient of the Need for Drug Therapy in Response to Atrial Fibrillation" which claimed the benefit of the U.S. provisional application 60/204,296 filed May 15, 2000. The Ser. No. 09/669,581 and 60/204,296 applications are both incorporated herein in their entireties by reference. The teachings of the '581 reference includes using a unipolar, high-output (e.g. 7.5 volts) stimulation pulse that will stimulate the pectoral muscle using only a tip electrode and the can of an implantable medical device. The invention also takes advantage of the teachings of U.S. Pat. No. 5,476,483 entitled "System and Method for Modulating the Base Rate During Sleep for a Wake-Responsive Cardiac Pacemaker" to Bornzin et al. which is incorporated herein in its entirety by reference. Embodiments of the U.S. Pat. No. 5,476,483 reference include using activity variance as a signal for determining the sleep state of a patient.

In accordance with embodiments of this invention, the notification signal 200 can be automatically provided by the device 10. The notification signal 200 is provided solely to the patient/implantee or, alternatively or in addition, to attending clinical personnel. Delivery of the notification signal 200 follows detection by the device 10 of a circumstance or condition indicating notification and, when provided to the implantee, is delivered in a manner to be readily noticed.

In one embodiment, the notification signal 200 comprises a series of N consecutive modified pacing pulses adapted to evoke pectoral muscle stimulation selected to be readily noticed by the patient. In one particular embodiment, the notification signal 200 comprises a series of N consecutive modified pacing pulses delivered via an electrode, such as one or more of the electrodes embodied within the right ventricular lead 30, and provided at approximately 7.5 volts with a pulse width of approximately 1 ms. It will be appreciated that in particular embodiments, the parameters of the modified pacing pulses comprising the notification signal 200, the delivery electrode(s), as well as the number N of individual pulses can be programmable in the device 10. In other embodiments, the notification signal 200 can be provided as disclosed in U.S. Pat. No. 6,546,288 which is incorporated herein in its entirety by reference.

One embodiment of the invention is selective timing or delay of delivery of the notification signals 200 to the patient until it is determined that the patient is in a desirable state for delivery of the notification signals 200. In embodiments wherein the notification signal 200 comprises a stimulation pulse provided by the device 10, the desirable state comprises time windows selected with respect to observed cardiac activity wherein the notification signals 200 are provided so as not to compete with cardiac function. In one embodiment, delivery of the notification signals is delivered based on observed R-waves and premature ventricular complexes (PVCs). In another embodiment, the notification signals are timed or triggered with respect to observed P-waves. Each of the N modified pacing pulses would thus be triggered by observed ventricular/atrial activity and delivered so as not to compete with intrinsic activity or therapeutic stimulations. In other embodiments, the notification signal 200 comprises an inhibited or asynchronous mode and the rate of the stimulation pulses is increased to provide overdrive pacing for the N cycles.

In one embodiment, the notification signal 200 is delivered in the ventricle and comprises a secondary pulse within 100 ms of an R-wave triggered or a capturing V-pulse, e.g. a forced Autocapture backup pulse, but at a significantly higher output than the standard backup pulse. In another embodiment, two stimulation pulses are safely delivered by reducing the AV delay, e.g. to 25-50 ms. In yet another embodiment, the notification signal 200 comprises three pulses delivered by reducing the AV delay and forcing a second ventricular pulse within 100 ms of the first.

In other embodiments, the notification signal 200 comprises stimulus pulses delivered to the atrium, e.g. when the device 10 is in AAI mode or if the notification signal 200 is desirably delivered both atrially and ventricularly. In embodiments wherein the device 10 comprises an ICD, the notification signal 200 can comprise pulses delivered between the SVC coil electrode 38 and the housing or case 40. In these embodiments, a pectoral implant site for the device 10 is preferred and the notification signal 200 is provided asynchronously.

In certain embodiments, the notification signal 200 is provided telemetrically, such as via the telemetry circuit 100 in communication with the external device 102. As previously described, the external device 102 can comprise a programmer. In these embodiments, attending clinical personnel can receive the notification signal 200 on the external device 102 and can further interrogate the device 10 for additional data and/or provide reprogramming to the device 10 if so indicated. In certain embodiments, the attending personnel can also obtain more detailed data from the device 10 via the communication link 104, such as more detailed data on the condition of the battery 110.

In other embodiments, the external device 102 comprises a wireless modem such that the notification signal 200 is communicated via the communication link 104 to the external device 102. In this embodiment, the external device 102 also comprises a communications network such that the notification signal 200 can be communicated and accessed remotely. Thus, in this embodiment, attending clinical personnel can receive the notification signal 200 via the external device 102 when they are not co-located with the patient. In yet other embodiments, the notification signal 200 comprises tactile and/or audible vibrations provided by the device 10 so as to be observable by the implantee.

As previously described, delivery of the notification signal 200 occurs when a desirable state exists. In embodiments wherein the notification signal 200 is provided to the patient, the desirable state comprises a waking state and, optionally, also a state of relative lack of strenuous physical activity. This embodiment of the invention is based on a calculation of a rest mode burden. This calculation takes advantage of circumstances where the patients go in and out of a relatively restful state many times throughout a day whether they are awake or asleep however under the observation that much more extended time will be spent in a rest state during periods of true sleep than during periods of relatively inactive wakefulness. Thus, delivery of the notification signal 200 is selected such that patient is awake to notice the notification signal 200 and, optionally, also not engaged in distracting strenuous activity that might mask or obscure the notification signal 200.

Figure 3:
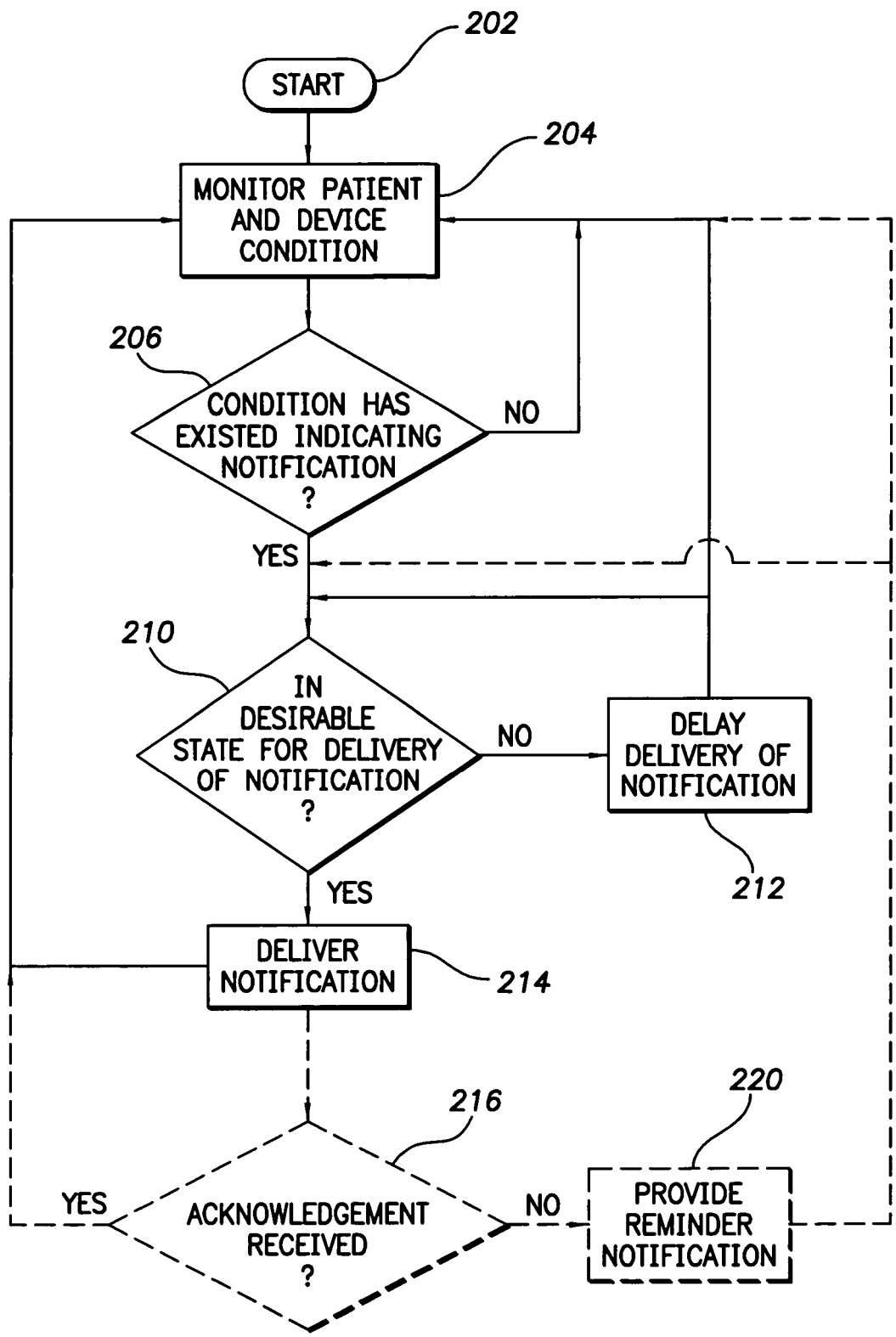
FIGS. 3 and 4A and 4B are flowcharts of embodiments of the operation of an implantable medical device with a notification system.

FIG. 3 is a flowchart of embodiments of the device 10 providing the notification signals 200 as previously described. This embodiment begins in a start state 202 which can include an implantation and programming procedure of the device 10 as is known in the art. An ongoing state 204 indicates ongoing monitoring of the patient's condition and can include periodic delivery of therapeutic stimulation by the device 10 as previously described. As previously mentioned, the device 10 is also capable of monitoring for conditions indicating delivery of a notification either to the patient and/or to attending clinical personnel. State 206 indicates an ongoing decision state whether such a condition has existed. Upon determination that one or more conditions has existed indicating notification, the device determines in state 210 whether a desirable state exists for delivery of such notification. As previously described, for notification of the patient, the desirable state can include a waking state, the determination of which will be described in greater detail below, and, in certain embodiments, determination of a desired point in the patient's cardiac cycle.

If the determination is made that the desirable state does not exist, state 212 follows wherein delivery of the notification is delayed. In various embodiments, this delay can vary between fractions of a second to the desirable point in the patient cardiac cycle to several hours where the determination is made that the patient is awake and alert. Once the determination is made in state 210 that the desirable state does exist, the notification signal 200 is delivered in state 214.

In certain embodiments, a decision state 216 follows wherein the device 10 makes a determination as to whether or not an acknowledgement signal has been received. State 216 provides the ability for a user to provide an acknowledgement signal to the device 10 to indicate that the notification signal 200 has been successfully received and acknowledged. Thus, an affirmative result of decision state 216 can indicate in certain embodiments that upon receipt of the notification signal 200 the patient has carried through with an indicated medication dosing, scheduled a follow-up visit with their physician, and/or performed other activity indicated by the notification signal 200 to provide a "clear" function for state 206. State 216 also provides the ability for a user to delay subsequent delivery of the notification signals 200 with another input, such as via the communication link 104 to acknowledge the condition indicating notification, but indicate a desire to delay reminder notifications. Thus, state 216 provides the ability for a user to "snooze" subsequent notifications.

In this embodiment, a negative result of decision state 216, e.g. a failure to receive the acknowledgement signal induces the device 10 to proceed to a state 220 where a follow-up or reminder notification is provided. In one embodiment, the reminder notification provided in state 220 is simply a repetition of a previous notification signal 200 delivered at a later time with a delay that can be programmable or dependent on user input. In this embodiment, the device 10 would proceed through the previously described states to re-monitor whether an acknowledgement signal is received in state 216. In other embodiments, the reminder or follow-up notification of signal 220 may comprise a repetition of a notification signal 200 but at revised parameters. In particular, the notification signals 200 provided as follow-up or reminder notifications in state 220 can comprise a notification signal 200 of greater magnitude, duration, and/or provided with different timing.

The reminder notifications of state 220 can also comprise combined notification signals 200, such as a combination of the stimulation pulses and vibrations as the notification signal 200. In certain embodiments, the notification signal 200 is progressively modified in successive occurrences of state 220 to improve the likelihood of the notification signals 200 being noticed. In certain embodiments, state 220 is subject to timeout or countout provisions as well as a maximum intensity or duration of provision of the notification signals 200 so as to avoid entrance of the device 10 into an endless loop where acknowledgement in state 216 is never received.

This embodiment provides the advantage of providing lower intensity notification signals 200 when adequate so as to conserve battery power with the ability to increase the intensity for more noticeable notification. In certain embodiments, the device 10 automatically evaluates the patient's activity level, such as via the physiologic sensor 108 and provides the notification signals 200 at an intensity level in state 214 that is automatically scaled with the evaluated activity so as to provide readily noticeable notification signals 200 and reduce drain on battery capacity.

In one embodiment, the acknowledgement signal monitored for in state 216 is provided via the communication link 104 to the telemetry circuit 100. In other embodiments, the acknowledgement signal is provided by a user bringing a magnet into adjacency with a magnetic switch 150 of the device 10. In this embodiment, the magnetic switch 150 comprises a magnetically operated reed switch of a type known in the art.

Figure 4A:
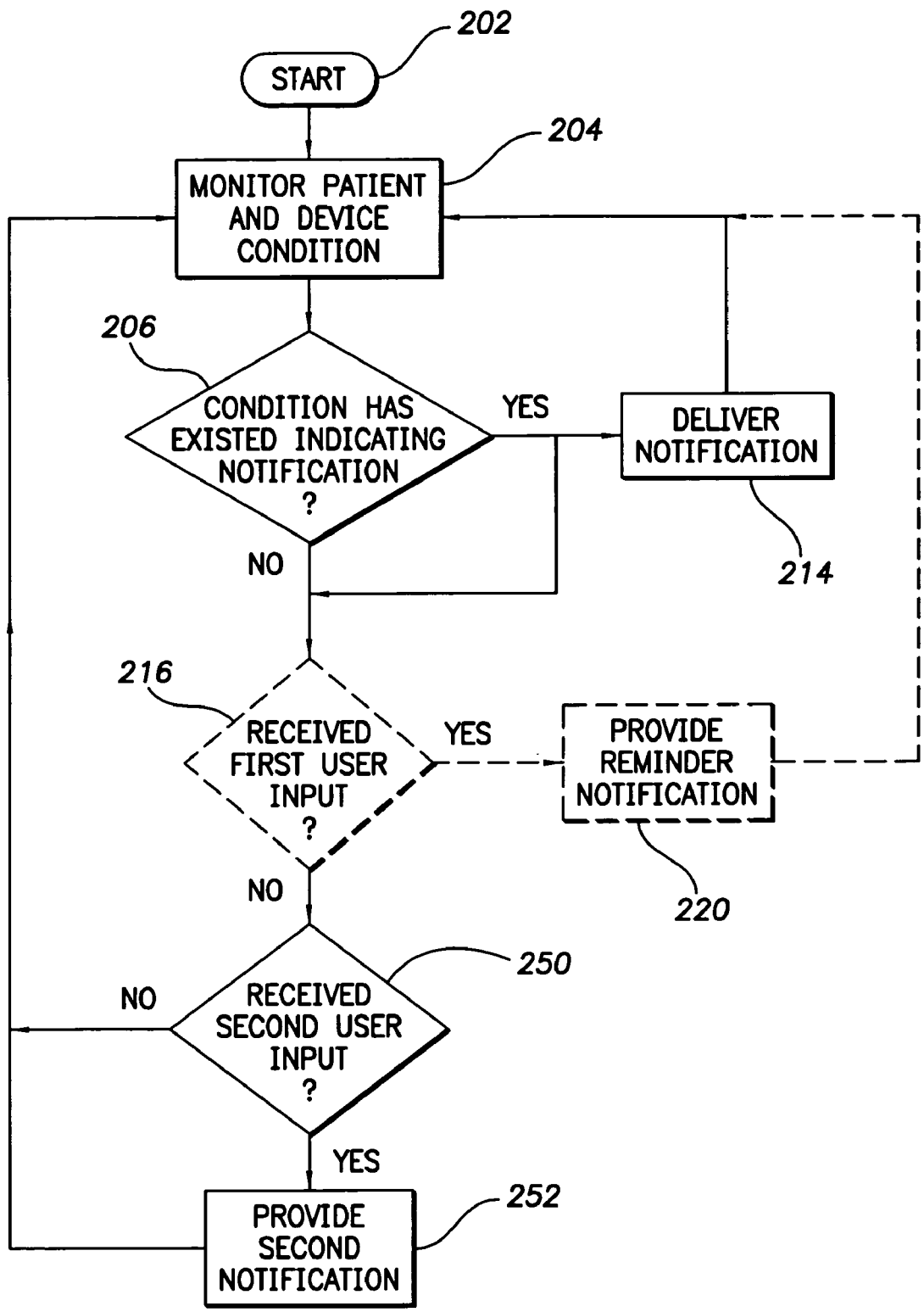

FIG. 4A illustrates another embodiment of the operation of the device 10 with provision for receipt and corresponding response to multiple-user inputs. This embodiment includes the states 202, 204, 206, and 214 with the optional inclusion of the acknowledgement decision state 216 with reminder or follow-up notification state 220 as previously described. In such embodiments, the acknowledgement signal monitored in state 216 comprises a first user input. This embodiment also includes a decision state 250 where a determination is made whether a second user input has been received. In these embodiments, the first user input can comprise a signal provided via one of the magnet switch 150 and the telemetry circuit 100 where the second input is provided via the other respectively. In other embodiments, a first user input comprises a first signal provided via either of the telemetry circuit 100 or magnet switch 150 and the second user input comprises a second signal provided respectively thereto. Thus, in one embodiment, a user may bring a magnet into adjacency with the magnet switch 150 for a brief period of time to provide the first user input and for a more extended period of time to provide the second user input. In another embodiment, the user may bring the magnet into adjacency with the magnet switch 150 a single time to provide the first user input and multiple times to provide the second user input.

In this embodiment, an affirmative result of decision state 250 results in provision of a second notification in state 252. In this embodiment, the second user input and corresponding second notification provided in state 252 provides different information than that provided with the notification delivered in state 214. In one embodiment, the notification delivered in state 214 comprises the notification signal 200 relating e.g. to an alert condition and the second notification provided in state 252 can provide other information, such as a report on battery status.

Thus, state 216 provides the capability for a user to provide a first user input to either acknowledge receipt of the notification of state 214 which provides the user the capability to either indicate that appropriate action has been taken, and/or to instruct the device 10 to delay delivery of follow-up or reminder notifications of state 220 for a determined period of time, e.g. a "snooze" function. This delay period is programmable in certain embodiments and can also be dependent on the user inputs. The ability is also provided for receipt of a second user input the receipt of which is monitored in state 250 to request a report or notification independently of the notification of state 214, 220.

Figure 4B:
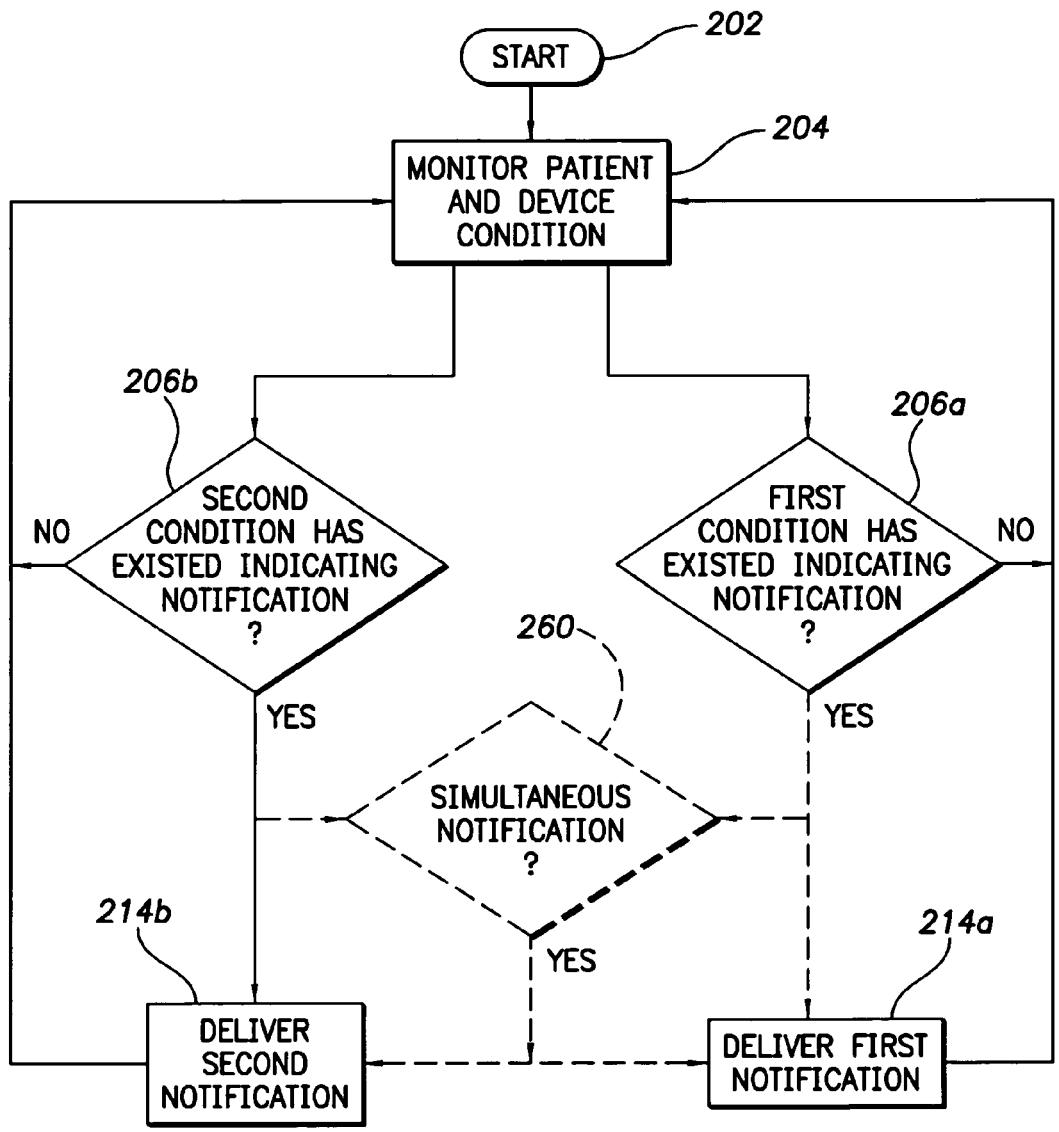

FIG. 4B illustrates another embodiment of the operation of the device 10 with provision for monitoring multiple conditions which may indicate notification and corresponding delivery of multiple notification signals 200 for different conditions that may occur. This embodiment includes the states 202 and 204 previously described. States 206*a* and 206*b* and 214*a* and 214*b* are substantially similar to the states 206 and 214 previously described, except that states 206*a* and 206*b* correspond to determining whether first and second different conditions have existed that indicate notification. States 214*a* and 214*b* indicate corresponding delivery of different notification signals 200 corresponding to the different conditions observed in states 206*a* and 206*b*.

In one embodiment, the notification signal 200 can adopt different specific parameters to provide distinguishable first and second notification signals 200 corresponding to different conditions in states 214*a* and 214*b*. For example, the previously mentioned five pulses can comprise a first notification signal 200 corresponding to a detection of AT/AF in state 206*a* and a series of twenty pulses can comprise a second notification signal 200 corresponding to a change in capture threshold determined in state 206*b*. In other embodiments, the device 10 provides one or more mechanical vibration patterns which can be audible and/or tactilely observable as notification signals 200. The device 10 can thus provide not only different numbers or patterns of a given base notification signal 200, but can also provide different base notification signals 200 to correspond to different conditions. For example, a first notification signal 200 comprising a series of five pulses can correspond to detection of AT/AF, detection of a high capture threshold results in a corresponding tactile vibration as a second notification signal 200, and a marked change in lead impedance would result in an audible beep or tone as a third notification signal 200.

An optional state 260 can be included in certain embodiments to determine whether first and second conditions are observed in states 206*a* and 206*b* which would indicate simultaneous, conflicting notification. If the determination of state 260 is affirmative, one of the notification signal 200 deliveries of state 214*a* or 214*b* can be delayed to avoid confusion on the part of the implantee due to delivery of multiple, simultaneous notification signals 200 or masking of one notification signal 200 by another. It will also be understood that the embodiments illustrated by and described with respect to FIG. 4B can be combined with the other embodiments of the invention disclosed herein.

Figure 5:
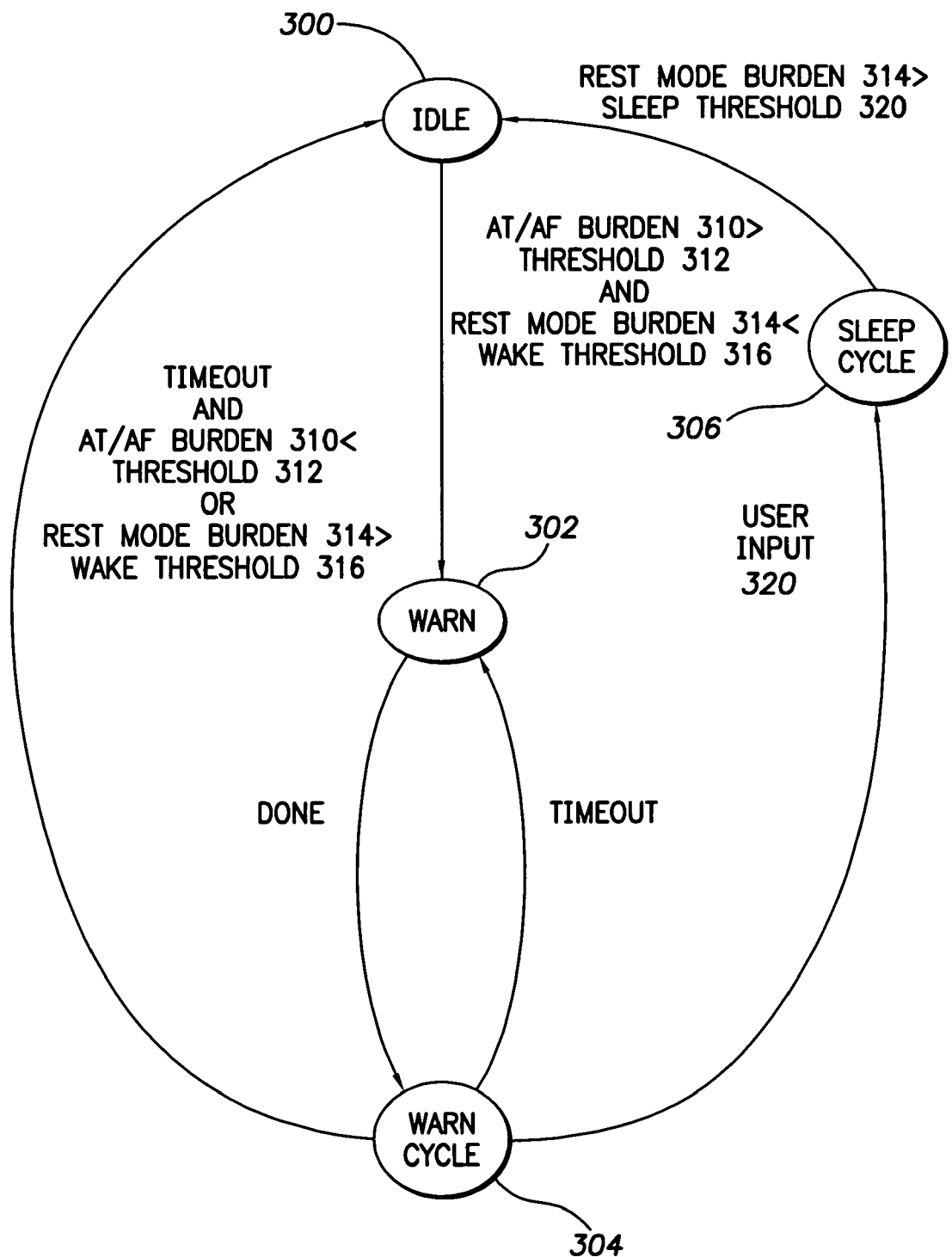
FIG. 5 is a state machine diagram of one embodiment of an implantable medical device with a notification system.

FIG. 5 illustrates one embodiment of a state machine for a device 10 having such a notification system. The embodiment described herein with respect to FIG. 5 will be with respect to one particular example of a notification condition and a desirable state for delivery of the notification, however such specific examples are provided for illustrative purposes and do not limit the scope of the invention. In this embodiment, state 300 indicates an idle state. In this state 300, the device 10 operates under the ongoing monitoring and selective generation and delivery of therapeutic stimulations as previously described, e.g. in state 202. However, the state 300 also indicates generally an observed circumstance of patient wakefulness and lack of a condition indicating generation and delivery of a notification signal 200.

A transition out of the idle state 300 to a warn state 302 occurs when a notification condition occurs, in this embodiment, when an AT/AF burden 310 is determined to be greater than an AT/AF burden threshold 312 which will be described in greater detail below. Briefly, the AT/AF burden 310 is a determined quantized parameter indicating the intensity or amount of observed AT/AF and the AT/AF burden threshold 312 is a determined threshold value indicating whether or not notification is to be performed.

The transition from idle state 300 to warn state 302 is also performed in this embodiment under an "AND" condition when a rest mode burden 314 is determined to be less than a wake threshold 316. These conditions will be described in greater detail below, however briefly the rest mode burden 314 indicates generally a determined amount of observed resting level of activity and the wake threshold 316 is a determined threshold separating active from rest states. In general, the transition from idle state 300 to warn state 302 occurs when the device 10 has observed a condition, such as sufficient AT/AF, to indicate delivery of a notification signal 200 AND that the patient is not in a sleep state so as to be likely to be able to notice delivery of a notification signal 200.

In this embodiment, the warn state 302 comprises certain temporary changes to the programming and stimulation delivery of the device 10. In this particular embodiment, the operating mode of the device 10 is temporarily switched to the DDT(R) mode triggering delivery of the notification stimulus substantially simultaneously with a sensed R wave. The ventricular pacing amplitude is temporarily set to 7.5 volts and the ventricle lead configuration to a unipolar setting. In this particular embodiment, five consecutive pacing pulses with these temporary settings are delivered and then the device 10 is returned to the previously programmed settings. When these actions are completed, indicated in the FIG. 5 by the "Done" transition, the device transitions to a warn cycle state 304.

In certain embodiments, the notification signals 200 are repeated periodically, for example hourly, provided the condition still exists indicating delivery of the notification signals 200. In these embodiments, the number of times that the notification signals 200 are repeated may also be defined and the number of repetitions as well as the interval therebetween may be programmable aspects of the notification signal 200.

The warn cycle state 304 provides the possibility for the device 10 operation to return to either of the two previously described idle 300 or warn 302 states as well as a sleep cycle state 306. In this particular embodiment, the AT/AF burden 310 is next evaluated one hour later. If the AT/AF burden 310 is less than the AT/AF burden threshold 3120R if the rest mode burden 314 is greater than the wake threshold 316, then the device 10 transitions to the idle 302 state.

In this embodiment, the sleep cycle state 306 is entered when a patient input parameter is programmed on and the device 10 receives a first patient input (such as monitored in state 216). In one embodiment, the first patient input comprises application of a magnet as previously described. The sleep cycle 306 provides the ability for a patient or clinician to selectively command the device 10 to forestall delivery of notification signals 200 when aware of an impending period of rest during which they would not wish to be disturbed. In this particular embodiment, the sleep cycle 306 automatically transitions back to the idle state 300 when the rest mode burden 314 is greater than the sleep wake threshold 316 indicating a return from a period of sleep to an awake state and the ongoing operation under the idle state 300 as previously described.

The patient input 320 also provides the ability for a user to inform the device 10 that the notification signal 200 has been received and noted. The patient input 320 can also provide the ability to inhibit follow-up delivery of notification signals 200. For example, the notification signal 200 may correspond to a condition indicating scheduling of a clinical visit and activation of the patient input 320 indicates to the device 10 that appropriate response has been taken and that no further delivery of notification signals 200 is needed for the particular condition. This aspect of the invention provides the advantage of saving limited battery power by inhibiting superfluous notification signals 200 as well as reducing any discomfort and distraction to the patient arising therefrom. It will be appreciated that the patient input 320 can be operated and provided by others than the implantee, such as attending clinical personnel.

Figure 6:
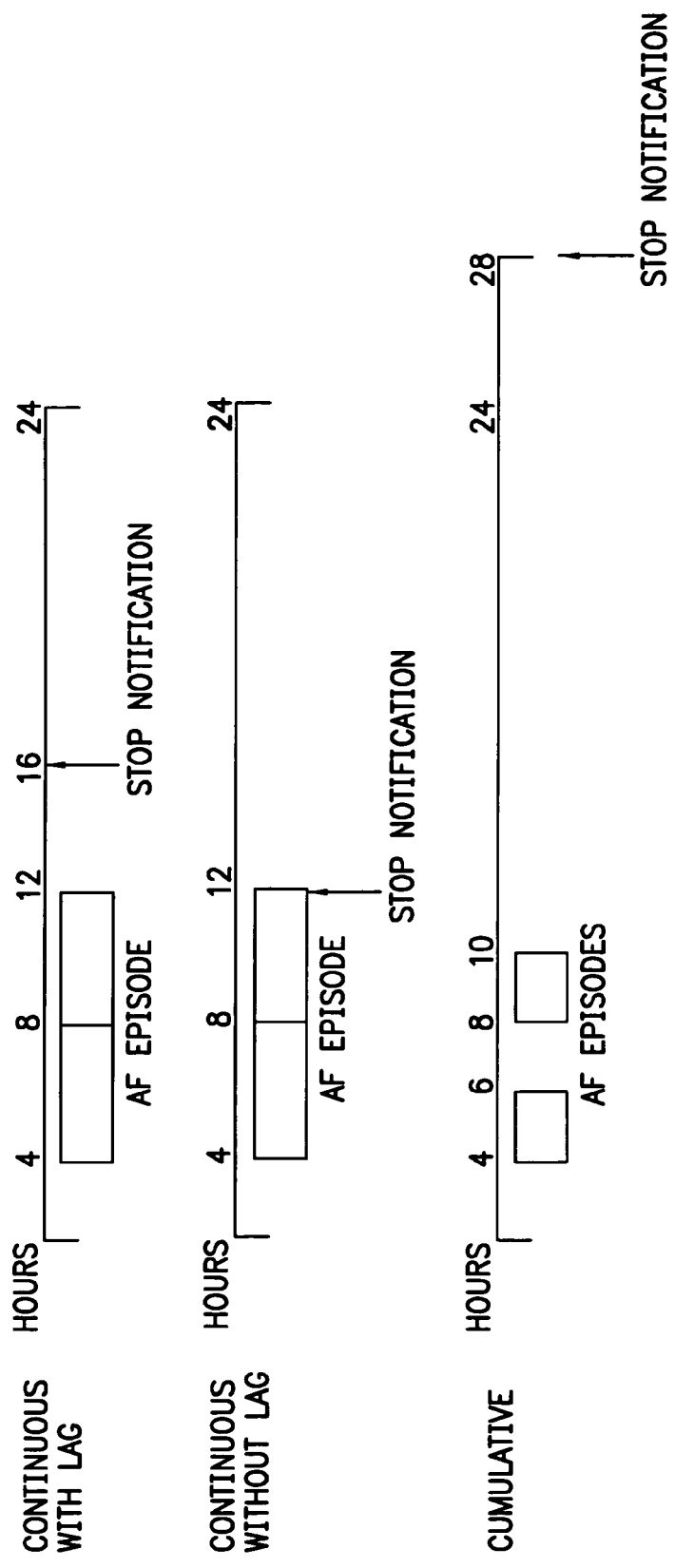
FIG. 6 is a timing diagram of embodiments of providing notification following immediately or a determined delay after a continuous period of AF as well as after a cumulative, non-continuous duration of AF episodes.

One embodiment of conditions leading to generation and delivery of a notification signal 200 will now be described in greater detail with respect to observed episodes of atrial tachycardia/atrial fibrillation (AT/AF). While this particular embodiment will be described with respect to AT/AF, it will be appreciated that a wide variety of other observed conditions can indicate notification in accordance with the invention and this description of AT/AF is simply one example. In this embodiment, determination of the AT/AF burden 310 can be determined under two different modalities which may be observed and determined concurrently as illustrated in FIG. 6.

One particular mode is observing for existence of a continuous period of time where AT/AF is detected. In one particular example, a continuous amount of time during which AT/AF is detected may be determined as defining the AT/AF burden 310. It will be appreciated that these continuous amounts of time may vary from patient to patient and/or may be programmable. In one particular example, the continuous amount of time to determine AT/AF burden 310 is set for X number of hours (e.g. 1, 2, 4, 12, 16, or 20 hours continuously).

A second mode under which the AT/AF burden 310 may be determined as a cumulative or proportional amount of time over a given period during which AT/AF is detected. For example, AT/AF burden 310 may be determined as the amount or proportion X of Y hours during which AT/AF is observed. For example, the AT/AF burden 310 may be determined as existence of tiered amounts of 4, 8, 12, 16, or 20 hours out of the last 24 hours. It will of course be appreciated that these particular values are exemplary and may also be programmable in the device 10. The AT/AF burden threshold 312 may also be programmable and as corresponding to either or both of the AT/AF burden 310 under the mode of a continuous amount of time and/or a cumulative or proportional amount of time as previously described. Again, the AT/AF burden threshold 312 is determined as the threshold above/below which generation and delivery of a corresponding notification signal 200 is or is not to be performed, e.g. the determination of state 206.

In one particular embodiment, the AT/AF burden 310 and burden threshold 312 are determined on a previous 48-hour history. In this embodiment, 48 bins are reserved in memory as a circular buffer with each bin representing one hour of time. An observed atrial-rate status, high atrial rate (HAR) or not is sampled every sixteen seconds and the count in the bin representing the current hour is incremented if there is an observed HAR. A count of 225 sixteen-second intervals represents 3,600 seconds or one hour. At the end of each hour, the AT/AF burden 310 status is assessed by totaling the counts in the bins representing the appropriate length of recent history and dividing by a maximum possible count.

Following are one embodiment of programming parameters that may be provided to the device 10 to facilitate implementation of aspects of the invention. It will be appreciated that these are examples of one embodiment and that additions or deletions may be made and that these examples are intended to be illustrative not restrictive.

AT/AF Burden Bin [48] (1 byte) (48 bins)

AT/AF Burden Bin Index (1 byte)

Set AT/AF Burden Bin[0-47]=0 and AT/AF Burden Bin Index=0 on Startup. Startup occurs when input data becomes available, such as in state 202. Every 16 seconds (e.g. every 8 2-second clocks), check the state of the input. If the current state of AT/AF Detection State Machine is "AT" or "AF" or "Post AF AT" (or Mode Switch Status="True"), then increment AT/AF Burden Bin[AT/AF Burden Bin Index] by one.

Every hour, beginning one hour after startup, increment AT/AF Burden Bin Index. When AT/AF Burden Bin Index would reach 48, set it instead to 0 thus implementing a circular buffer. Every hour, beginning a Burden Threshold Basis hours after startup, total the counts in the most recent Burden Threshold Basis bins. Divide this total by the number of possible counts (Burden Threshold Basis*225) to obtain the AT/AF Burden 310. Compare the calculated AT/AF Burden to the programmed Burden Threshold and act on the result of the comparison according to the state machine logic as previously described.

As previously described, embodiments of the invention include determination of a desirable state for delivery of the notification signal 200. In this embodiment, the Rest Mode Burden 314 algorithm adjusts its activity variance threshold automatically and individually for each patient so that, on average, Rest Mode is indicated for approximately 8 hours of each day. Ideally, Rest Mode is indicated for a single contiguous 8-hour period each day corresponding to a period of time when the patient is in bed. However, depending on patient lifestyle and/or occasional deviations from a daily routine, this 8 hours may be greater or lesser or broken up into smaller periods distributed throughout any given day. A consolidated period of rest, however, will consistently result in a much higher percentage of time for which Rest Mode is indicated during that period, compared to a period of relative activity. It is generally during these consolidated periods of rest that the device 10 postpones delivery of the patient notification signal 200 of a condition, such as detection of AF, which indicates patient notification.

The Rest Mode algorithm makes a determination every 30 seconds as to whether or not to indicate Rest Mode. This Rest Mode Burden 314 calculation maintains a recent history of these Rest Mode status determinations made over the last 30 minutes. The proportion of determinations over any given period within this hour constitutes the Rest Mode Burden 314 for that period and is calculated on demand.

This embodiment assumes that 1 byte will record the result of each of the 60 most recent Rest Mode status determinations. Obviously, many other implementations are possible. One would be to use single bits to record the status determinations.

Note that, in certain embodiments, Atrial Defibrillation therapy may require up to 8 hours of Rest Mode Status history. Following are examples of parameters and programming instructions for one embodiment of determination of the Rest Mode.

Rest Mode Burden Bin [60] (1 byte)(60 bins)

Rest Mode Burden Bin Index (1 byte)

On startup, set Rest Mode Burden Bin[0-59]=0 and Rest Mode Burden Bin Index=0. Startup occurs when Rest Mode status determinations begin, such as in state 202.

Each time the Rest Mode status is determined, record the status (True if Rest Mode is indicated or False if not) in Rest Mode Burden Bin[Rest Mode Burden Bin Index] and increment Rest Mode Burden Bin Index. When Rest Mode Burden Bin Index would reach 60, set it instead to 0, thus implementing a circular buffer.

Also each time the Rest Mode status is determined, determine whether or not Rest Mode Burden is below Wake Threshold 316. In one embodiment, this is defined as follows: If less than 9 of the most recent 60 Rest Mode status determinations (i.e. <15% over the last 30 minutes) were True, then the Rest Mode Burden 314 is below the Wake Threshold 316. Otherwise, Rest Mode Status is above the Wake Threshold 316.

Also each time the Rest Mode status is determined (as applicable), determine whether or not Rest Mode Burden 314 is above Sleep Threshold 320. This is defined as follows: If more than 51 of the most recent 60 Rest Mode status determinations (i.e. >85% over the last 30 minutes) were True, then the Rest Mode Burden 314 is above the Sleep Threshold 320. Otherwise, the Rest Mode Burden 314 is below the Sleep Threshold 320.

FIG. 6 illustrates a further embodiment of the invention providing the versatility to program a duration of time following the termination of a condition indicating notification, such as a continuous episode of AF whereby the notification signal 200 would continue to be provided until the expiration of such a duration of time. FIG. 6 illustrates three timelines, each depicting a scenario for delivery of the notification signals 200. In each of these three embodiments, an AF episode begins at T=4 hours.

In the first and second embodiments, the AF episode goes on continuously for eight hours. In these two embodiments, four continuous hours in AF are required to indicate notification, e.g. to return an affirmative decision in state 206. Thus, in these embodiments, notification would be indicated beginning at T=8 hours. In the first embodiment, there is an optional "lag" of provision of the notification signals 200 of four hours, so notification continues until T=16 hours. In the second embodiment, there is not lag, so delivery of the notification signals 200 ends substantially immediately when the episode ends, e.g. at T=12 hours.

The third embodiment illustrated in FIG. 6 depicts the operation of a cumulative AF threshold programmed to notify with four of twenty-four hours cumulative time in the AF. Two 2-hour duration episodes begin at T=6 and T=8 hours. Notification begins at T=10 hours and continues until T=28 hours, e.g. until the first episode begins to fall out of the 24-hour window during which time AF is accumulated.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. An implantable medical device comprising:
   a controller;
   at least one cardiac sensing electrode providing cardiac sensed signals to the controller;
   a stimulation pulse generator receiving control signals from the controller; and
   at least one cardiac stimulation electrode connected to the stimulation pulse generator to provide indicated cardiac stimulation therapy wherein the controller evaluates the cardiac signals received from the at least one cardiac sensing electrode and, upon determination that at least one condition indicating notification has existed and that a desirable state for receipt of a notification signal exists, induces the device to deliver the notification signal;
   wherein the notification signals at least partially comprise cardiac stimulation pulses delivered by the stimulation pulse generator and the at least one cardiac stimulation electrode.

2. The device of claim 1, wherein the desirable state comprises a waking state of a patient.

3. The device of claim 2, wherein the desirable state further comprises an absence of strenuous physical activity.

4. The device of claim 1, wherein, when the device determines that the at least one condition indicating notification has existed but the desirable state does not exist, the device delays delivery of the notification signal until such time as the device determines that the desirable state exists.

5. The device of claim 1, wherein the device can deliver multiple notification signals over a period of time corresponding to a given notification condition.

6. The device of claim 1, wherein the condition indicating notification comprises detection of an episode of atrial tachycardia.

7. The device of claim 1, wherein different notification signals are provided for different notification conditions.

8. The device of claim 1, wherein the notification signals are of variable intensity and wherein the device automatically evaluates a patient's activity and automatically adjusts the intensity of the notification signals to correspond to the evaluated activity.

9. An implantable medical device comprising:
   a controller;
   at least one cardiac sensing electrode providing cardiac sensed signals to the controller;
   a stimulation pulse generator receiving control signals from the controller; and
   at least one cardiac stimulation electrode connected to the stimulation pulse generator so as to provide indicated stimulation therapy to the heart wherein the controller evaluates the signals received from the at least one cardiac sensing electrode and, upon determination that a first condition indicating notification has existed, induces the device to deliver at least a first notification signal and, upon determination that a second condition indicating notification has existed, induces the device to deliver a different second notification signal;
   wherein at least one of the first and second notification signals comprises delivery of one or more electrical stimulation pulses to the heart via the stimulation pulse generator and at least one cardiac stimulation electrode.

10. The device of claim 9, wherein the device evaluates whether simultaneous inducement of delivery of the first and second notification signals is indicated and, if so, inhibits delivery of one of the first and second notification signals.

11. The device of claim 9, wherein the first condition comprises a sustained episode of AT/AF.

12. The device of claim 9, further comprising a user input wherein delivery of the second notification signal follows receipt of a signal from the user input.

* * * * *

UNITED STATES PATENT AND TRADEMARK OFFICE
CERTIFICATE OF CORRECTION

PATENT NO. : 7,606,618 B1  Page 1 of 1
APPLICATION NO. : 11/400114
DATED : October 20, 2009
INVENTOR(S) : Bornzin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 742 days.

Signed and Sealed this

Twelfth Day of October, 2010

David J. Kappos
*Director of the United States Patent and Trademark Office*